United States Patent
Kim et al.

(10) Patent No.: US 9,694,008 B2
(45) Date of Patent: Jul. 4, 2017

(54) FAST-DISSOLVING ORAL FILM PREPARATION COMPRISING ARIPIPRAZOLE

(71) Applicant: CMG Pharmaceutical CO., LTD., Seoul (KR)

(72) Inventors: Yong Soo Kim, Pyeongtaek-si (KR); Jun Ho Shin, Ansan-si (KR)

(73) Assignee: CMG Pharmaceutical Co., LTD., Seoul (KR)

( * ) Notice: Subject to any disclaimer, the term of this patent is extended or adjusted under 35 U.S.C. 154(b) by 0 days.

(21) Appl. No.: 14/419,231

(22) PCT Filed: Aug. 7, 2013

(86) PCT No.: PCT/KR2013/007129
§ 371 (c)(1),
(2) Date: Feb. 2, 2015

(87) PCT Pub. No.: WO2014/025206
PCT Pub. Date: Feb. 13, 2014

(65) Prior Publication Data
US 2015/0196558 A1    Jul. 16, 2015

(30) Foreign Application Priority Data
Aug. 8, 2012  (KR) .................. 10-2012-0086749

(51) Int. Cl.
*A61K 31/496* (2006.01)
*A61K 9/00* (2006.01)
(Continued)

(52) U.S. Cl.
CPC ............ *A61K 31/496* (2013.01); *A61K 9/006* (2013.01); *A61K 47/12* (2013.01); *A61K 47/22* (2013.01); *A61K 47/32* (2013.01); *A61K 47/38* (2013.01)

(58) Field of Classification Search
None
See application file for complete search history.

(56) References Cited

U.S. PATENT DOCUMENTS

| 4,734,416 A | 3/1988 | Banno et al. |
| 5,006,528 A | 4/1991 | Oshiro et al. |

(Continued)

FOREIGN PATENT DOCUMENTS

| EP | 1145711 A1 | 10/2001 |
| KR | 10-2001-0096450 A | 11/2001 |

(Continued)

OTHER PUBLICATIONS

Monali Bhosle et al. "Difficult to swallow: patient preferences for alternative valproate pharmaceutical formulations" Patient Preference and Adherence, vol. 3, pp. 161-171 (Jun. 25, 2009).

(Continued)

*Primary Examiner* — Jianfeng Song
(74) *Attorney, Agent, or Firm* — Novick, Kim & Lee, PLLC; Jae Youn Kim

(57) ABSTRACT

The present invention relates to an orally fast dissolving film formulation including aripiprazole. The orally fast dissolving film formulation includes aripiprazole or a pharmaceutically acceptable salt thereof and an organic acid. The orally fast dissolving film formulation has a pH in the range of 4.7 to 6.0. The orally fast dissolving film formulation may further include a film base polymer. The orally fast dissolving film formulation has a high dissolution rate, causes no risk of damage to oral tissues, masks a bitter taste of aripiprazole, and gives a good feeling upon taking.

4 Claims, 2 Drawing Sheets

(51) Int. Cl.
  *A61K 47/38* (2006.01)
  *A61K 47/32* (2006.01)
  *A61K 47/12* (2006.01)
  *A61K 47/22* (2006.01)

(56) References Cited

U.S. PATENT DOCUMENTS

2010/0216783 A1* 8/2010 Bhat ............... A61K 31/538
                                                            514/230.5
2012/0156229 A1* 6/2012 Park ............... A61K 9/0056
                                                            424/184.1

FOREIGN PATENT DOCUMENTS

| KR | 10-2003-0096332 A | 12/2003 |
| KR | 10-2010-0138768 A | 12/2010 |
| KR | 10-2011-0028179 A | 3/2011 |
| KR | 10-1043866 B1 | 6/2011 |

OTHER PUBLICATIONS

Yeon-Ji Oh. "Inorganic Drug Delivery System for Poorly Water-soluble Drug and Its Bioequivalence Study" Research paper for master's degree, Department of Chemistry and Nano Science, Ehwa Woman's University (Dec. 2010).

Takayuki Yoshida et al. "Mechanism of controlled drug release from a salting-out taste-masking system" Journal of Controlled Release, vol. 131, pp. 47-53 (Jul. 2008).

Dong-Gu Seo. "Measurement of intra-oral pH and recovery speed of favorite drinks by telemetry method" Research paper for master's degree, Department of Dentistry, Yonsei University (Aug. 2005).

Mihajlovic, T. et al. "Improvement of aripiprazole solubility by complexation with (2-hydroxy) propyl-β-cyclodextrin using spray drying technique", Jun. 2012, AAPS PharmSciTech, vol. 13, No. 2, pp. 623-631.

* cited by examiner

FAST-DISSOLVING ORAL FILM PREPARATION COMPRISING ARIPIPRAZOLE

TECHNICAL FIELD

The present invention relates to an orally fast dissolving film formulation including aripiprazole.

BACKGROUND ART

Aripiprazole is a pharmaceutical compound having the IUPAC name 7-{4-[4-(2,3-dichlorophenyl)piperazin-1-yl]butoxy}-3,4-dihydroquinolin-2(1H)-one, which is represented by Formula 1:

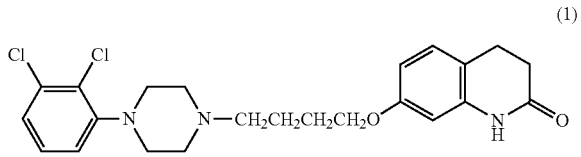

Aripiprazole is a dopaminergic neurotransmitter antagonist. Aripiprazole belongs to a group of carbostyril derivatives that can be used as atypical antipsychotics and antidepressants for schizophrenia, bipolar disorder, clinical depression, and the like (Patent Documents 1 and 2).

Aripiprazole is already known in the literature and more detailed pharmacological mechanisms, pharmacokinetics, synthesis methods, and side effects thereof can be understood from the disclosures of known references, for example, Non-Patent Document 1. Thus, Non-Patent Document 1 is incorporated herein by reference in its entirety and the following references are also incorporated herein by reference in their entireties.

Aripiprazole formulations in the form of tablets are widely commercially available (Abilify™, Otsuka Pharmaceutical Co.). For more successful treatment for schizophrenia, easy-to-take formulations are used in preference to swallowing tablets. That is, patients prefer orally disintegrating formulations to tablets and oral solutions that are difficult to swallow (Non-Patent Document 2).

In view of this, antipsychotics including aripiprazole as an active ingredient are presented in the form of orally disintegrating formulations, such as chewable tablets and rapidly dissolving films, as well as swallowing tablets. Conventional orally disintegrating formulations can be understood, for example, from Patent Document 3, which discloses a flash-melt oral dosage formulation of aripiprazole.

Orally disintegrating formulations of aripiprazole increase the convenience of administration for patients but cause the patients to feel bitterness peculiar to aripiprazole, resulting in an unfavorable feeling upon taking (Non-Patent Document 3).

To solve such problems, there have been developed, for example, techniques for encapsulating aripiprazole with polymeric materials (see Non-Patent Document 4) and techniques for constituting hybrid systems of aripiprazole with layered clay materials to suppress dissolution of the aripiprazole in the oral cavity (for example, Patent Document 4 discloses an aripiprazole-bentonite-AEA (polyvinyl acetaldiethyl-acetate) hybrid for masking a bitter taste of aripiprazole). However, these techniques have the problems of low dissolution rate and bioavailability of aripiprazole.

The problems of the prior art are explained by the fact that aripiprazole per se has a very low solubility in water (about 0.00001 w/v % at 25° C.), which directly leads to low bioavailability (see Non-Patent Document 5). Another reason is that when the dissolution of aripiprazole in the oral cavity is suppressed for the purpose of masking a bitter taste of aripiprazole, the dissolution rate of aripiprazole is considerably reduced, eventually increasing the possibility of poor bioavailability.

The low solubility of aripiprazole affects the dissolution rate of aripiprazole, leading to poor bioavailability. In this regard, an improvement in the solubility of aripiprazole is considered a very important technical solution in aripiprazole formulations, apart from bitterness masking.

The solubility of aripiprazole is pH-dependent and decreases with increasing pH. Particularly, it was found that aripiprazole has poor bioavailability at a pH exceeding 5 due to its low solubility (see Non-Patent Document 5).

Thus, most conventional aripiprazole formulations have been designed to be dissolved in low pH environments or have relatively low pH values.

Unlike a swallowing tablet or an oral solution whose retention time in the oral cavity is very short, an orally disintegrating formulation, particularly an orally fast dissolving film formulation, stays in the oral cavity for a relatively long time because the drug tends to disintegrate in the oral cavity, and therefore, its low pH causes serious damage to the oral tissues.

Particularly, teeth were found to undergo enamel demineralization at a pH of 5.7 or less, which is a cause of dental caries (see Non-Patent Document 6 and Non-Patent Document 7). For this reason, pH 5.7 is a critical point where teeth begin to decay and is considered as a reference point to determine what food causes tooth decay.

Particularly, aripiprazole is mainly prescribed for schizophrenia. Schizophrenia is treated by administration of a suppressive drug over a long period of time. The long-term administration of a formulation having a low pH inevitably causes damage to oral tissues such as teeth.

Under such circumstances, there is an urgent need for an orally fast dissolving film formulation that does not deteriorate the dissolution rate of aripiprazole while maintaining its pH at a level where the risk of dental caries in the mouth can be avoided.

There is another urgent need for an orally fast dissolving film formulation that can mask bitterness of aripiprazole without deteriorating the dissolution rate of aripiprazole.

PRIOR ART DOCUMENTS

Patent Documents (Patent Document 0001) U.S. Pat. No. 4,734,416 B
(Patent Document 0002) U.S. Pat. No. 5,006,528 B
(Patent Document 0003) EP 1145711 A1
(Patent Document 0004) KR 10-1125210 B1

Non-Patent Documents (Non-Patent Document 0001) Wikipedia, "Aripiprazole", http://en.wikipedia.org/wiki/Aripiprazole#cite_notepatent_5006528-50, visited on Jul. 10, 2012
(Non-Patent Document 0002) Bhosle M, Benner J S, DeKoven M, Shelton J. Patient Preference Adherence 2009; 3:161-171

(Non-Patent Document 0003) O, Yeon-ji, 「Inorganic drug delivery system for poorly water-soluble drug and its bioequivalence study」, Research paper for master's degree, Ewha Womans University, 2011, pp. 2-3

(Non-Patent Document 0004) Yoshida T, Tasaki H, Maeda A, Katsuma M, Sako K, Uchida T. J Control Release 2008; 131:47-53

(Non-Patent Document 0005) U.S. Food and Drug Administration (FDA), 「21-436 Abilify Clinical Pharmacology Biopharmaceutics Review」, http://www.fda.gov/default.htm, visited on Jul. 10, 2012

(Non-Patent Document 0006) Feagen F F, Gray J A: Discussion, Caries Res 11: 79-83, 1977

(Non-Patent Document 0007) S E O Dong-gu, 「Measurement of intra-oral pH and recovery speed of favorite drinks by telemetry method」, Research paper for master's degree, Yonsei University, 2005

DETAILED DESCRIPTION OF THE INVENTION

Problems to be Solved by the Invention

It is a first object of the present invention to provide an orally fast dissolving film formulation that has a high dissolution rate without the risk of damage to oral tissues. In connection with this object, the present inventors have found that when the pH of an oral formulation including aripiprazole is adjusted to a predetermined level by the addition of an organic acid, a high dissolution rate of the aripiprazole is achieved without the risk of damage to oral tissues. Based on this finding, the present invention has been accomplished.

It is a second object of the present invention to provide an orally fast dissolving film formulation that has a high dissolution rate and can mask a bitter taste of aripiprazole, giving a good feeling upon taking. In connection with this object, the present inventors have found that when a combination of an organic acid, sucralose, and acesulfame potassium is administered, an unpleasant taste of aripiprazole can be effectively masked. Based on this finding, the present invention has been accomplished.

Means for Solving the Problems

According to one aspect of the present invention, there is provided an orally fast dissolving film formulation including aripiprazole or a pharmaceutically acceptable salt thereof and an organic acid wherein the film formulation has a pH in the range of 4.7 to 6.0.

In the present invention, the organic acid is selected from citric acid, acetic acid, maleic acid, lactic acid, tartaric acid, ascorbic acid, adipic acid, succinic acid, fumaric acid, and mixtures thereof.

In the present invention, the organic acid is citric acid or tartaric acid.

In the present invention, the citric acid is included in an amount of 0.2 to 1.0 part by weight, based on the total weight of the orally fast dissolving film formulation.

In the present invention, the orally fast dissolving film formulation further includes a sweetening agent including sucralose and acesulfame potassium.

In the present invention, the orally fast dissolving film formulation further includes a film base polymer essentially including hydroxypropyl methylcellulose and optionally polyvinyl alcohol.

In the present invention, the orally fast dissolving film formulation has a pH in the range of 5.7 to 6.8 when dissolved in the oral cavity.

Effects of the Invention

The orally fast dissolving film formulation of the present invention has a high dissolution rate, causes no risk of damage to oral tissues, and masks a bitter taste of aripiprazole, giving a good feeling upon taking.

MODE FOR CARRYING OUT THE INVENTION

Figure 1:
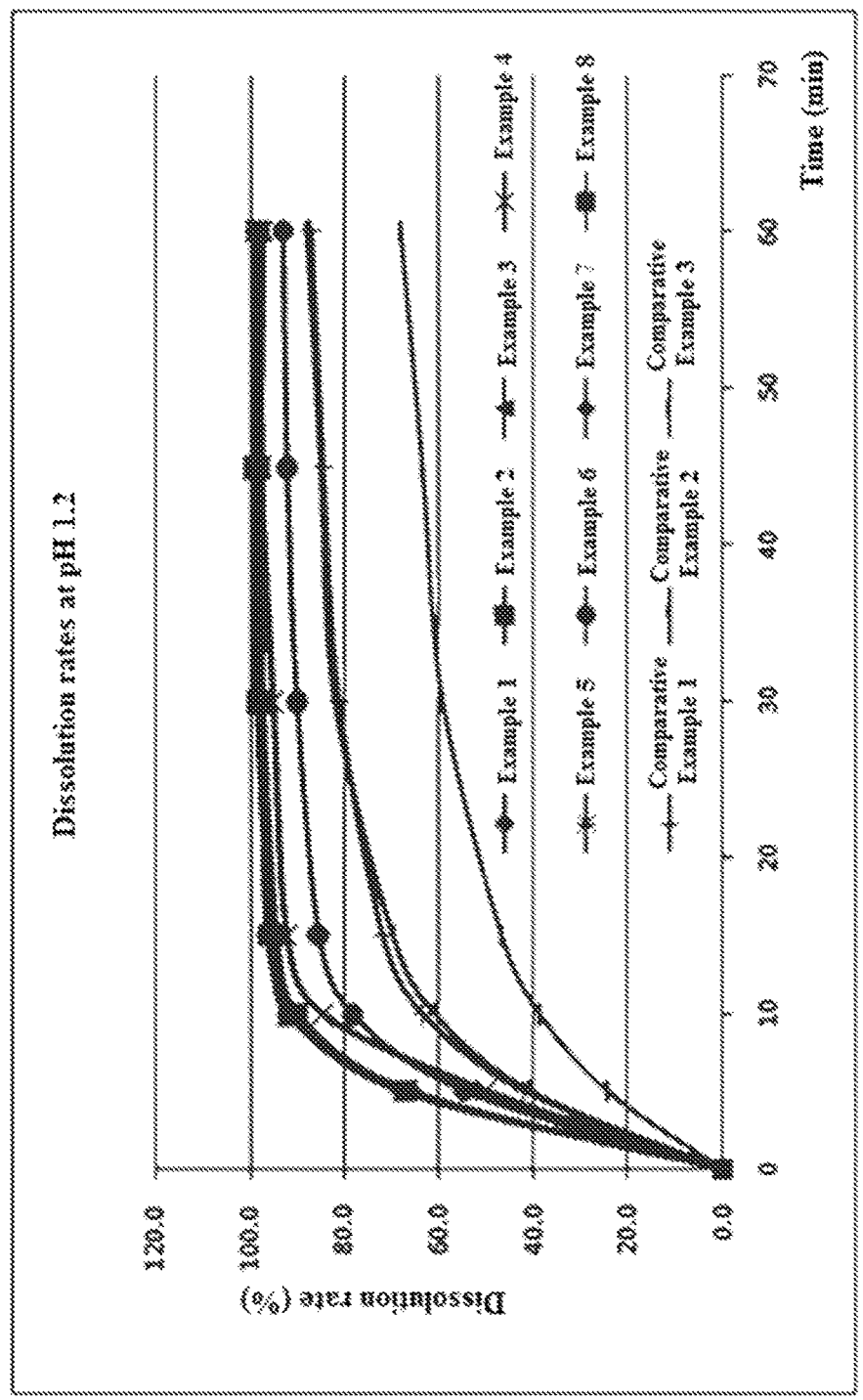
FIG. 1 is a graph showing the dissolution rates of orally fast dissolving film formulations produced in Examples 1-8 and Comparative Examples 1-3 at a pH of 1.2.

The present invention will now be described in detail.

In one aspect, the present invention provides an orally fast dissolving film formulation including aripiprazole or a pharmaceutically acceptable salt thereof and an organic acid wherein the film formulation has a pH in the range of 4.7 to 6.0.

The aripiprazole may be in free form or may form an acid addition salt with a pharmaceutically acceptable acid. Examples of such acids include, but are not necessarily limited to, sulfuric acid, nitric acid, hydrochloric acid, phosphoric acid, hydrobromic acid, acetic acid, p-toluenesulfonic acid, methanesulfonic acid, oxalic acid, maleic acid, fumaric acid, malic acid, citric acid, tartaric acid, succinic acid, ascorbic acid, adipic acid, lactic acid, and benzoic acid.

The organic acid lowers the pH of the orally fast dissolving film formulation to increase the solubility of the aripiprazole, contributing to an improvement in the dissolution rate of the aripiprazole. Other roles of the organic acid are to promote the secretion of saliva in the mouth and to impart a sour taste to the orally fast dissolving film formulation, allowing a taker to be less sensitive to bitterness peculiar to the aripiprazole.

The organic acid may be the same as or different from an acid forming the salt with the aripiprazole.

The organic acid is preferably an acid derived from food and may be, for example, selected from citric acid, acetic acid, maleic acid, lactic acid, tartaric acid, ascorbic acid, adipic acid, succinic acid, fumaric acid, and mixtures thereof. More preferably, the organic acid is citric acid or tartaric acid. The food-derived organic acid is effective in promoting the secretion of saliva in the mouth of a patient, enabling the patient to take the orally fast dissolving film without water, and serves to prevent the intra-oral pH from being excessively lowered, which will be understood from the examples section that follows. That is, the pH of the film decreases gradually with increasing amount of the organic acid added but the intra-oral pH is not lowered in proportion to the pH of the film due to the effect of the organic acid to increase the secretion of saliva. Further details will be understood from the following examples section, including experimental examples.

The citric acid is preferably included in an amount of 0.2 to 1.0 part by weight, based on the total weight of the orally fast dissolving film formulation. The presence of the citric acid in an amount of less than 0.2 parts by weight leads to a reduction in the solubility of the aripiprazole, resulting in a low dissolution rate of the aripiprazole, and is unsatisfactory in saliva secretion. Meanwhile, the presence of the citric acid in an amount exceeding 1.0 part by weight reduces the intra-oral pH to less than 5.7, causing undesirable damage to oral tissues, such as dental caries. Further details will be understood from the examples section that follows.

The orally fast dissolving film formulation of the present invention may further include a sweetening agent. The sweetening agent serves to mask a bitter taste.

The sweetening agent includes sucralose and acesulfame potassium as essential ingredients.

The gustatory response of the sweetening agent in the oral cavity varies slightly depending on the ingredients of the sweetening agent. The acesulfame potassium is first exhibited due to its faster gustatory response and the effect of the sucralose follows, so that the sweetening agent can effectively mask a bitter taste over the entire period during which the formulation is disintegrated in the mouth.

The weight ratio of the sucralose to the acesulfame potassium is preferably from 1:1 to 1:2.

The sweetening agent is preferably included in an amount of 0.5 to 5.0 parts by weight, based on the total weight of the orally fast dissolving film formulation.

The sweetening agent may further include a sweetener. Non-limiting examples of such sweeteners include L-menthol, xylitol, aspartame, saccharin salts, neotame, cyclamate salts, thaumatin, Luo han guo extract, licorice extract, sugar, glucose, maltose, oligosaccharides, dextrin, invert sugar, fructose, lactose, galactose, starch syrup, sorbitol, maltitol, erythritol, hydrogenated starch syrup, mannitol, and trehalose. These sweetening agents may be used alone or as a mixture thereof.

The orally fast dissolving film formulation of the present invention further includes a film base polymer.

The film base polymer is preferably a water-soluble polymer because the formulation should be disintegrated by saliva in the mouth.

The water-soluble polymer may be selected from carboxymethylethylcellulose, microcrystalline cellulose, hydroxypropyl methylcellulose phthalate, hydroxypropyl methylcellulose, hydroxypropyl cellulose, polyvinylpyrrolidone, polyvinyl alcohol, polyvinyl alcohol-polyethylene glycol block copolymers, xanthan gum, guar gum, starch, modified starch, gelatinized starch, and mixtures thereof. The water-soluble polymer is preferably selected from hydroxypropyl methylcellulose, hydroxypropyl cellulose, polyvinylpyrrolidone, polyvinyl alcohol, polyvinyl alcohol-polyethylene glycol block copolymers, and mixtures thereof. The water-soluble polymer is more preferably selected from hydroxypropyl methylcellulose, polyvinyl alcohol, polyvinyl alcohol-polyethylene glycol block copolymers, and mixtures thereof.

The pH of the orally fast dissolving film formulation is preferably in the range of 4.7 to 6.0. Below pH 4.7, there is a risk that oral tissues may be damaged. Meanwhile, above pH 6.0, the dissolution rate of the aripiprazole may deteriorate undesirably. Further details will be understood from the examples section that follows.

Preferably, the film base polymer essentially includes hydroxypropyl methylcellulose and optionally polyvinyl alcohol. The final pH of the film formulation may vary depending on the kind of the film base polymer. Further details will be understood from the examples section that follows.

There is no restriction on the method for producing the orally fast dissolving film of the present invention. For example, the orally fast dissolving film of the present invention may be produced by a method including the following processing steps:

(1) Preparation of solutions a) Preparation of first solution: polyvinyl alcohol (PVA) as a water-soluble polymer is completely dissolved in warm water.

b) Preparation of second solution: aripiprazole as an active ingredient and citric acid are mixed in ethanol using a homogenizer.

c) Preparation of third solution: the first solution is mixed with additives such as hydroxypropyl methylcellulose (HPMC) as a water-soluble polymer, Polyethylene Glycol 400, glycerin, a pigment, and a sensitizer.

d) Preparation of fourth solution: the third solution is mixed with the second solution to prepare a fourth solution.

(2) Molding

The fourth solution is filtered, fed into a molding machine, and molded into a film. The temperature of the molding machine is from 50 to 120° C. and the film is passed through a belt drum dryer. The film is produced in the form of a roll.

(3) Aging

The film is aged at 30 to 70% relative humidity for about 1 to about 10 days. As a result, the film contains water in an amount sufficient for slitting or cutting. At this time, the water content is preferably 5% or less. The method may further include the following processing steps.

(4) Cutting

The aged film is slit into smaller rolls, cut into desired sizes, and filled in small containers or aluminum packaging papers.

(5) Packaging

For commercialization, the filled containers or packaging papers are packaged in a small box or are blister packed.

The fast dissolving film formulation thus produced is rapidly disintegrated and dissolved by saliva in the mouth without the need to drink water. Therefore, the film formulation can be easily administered to patients, particularly the elderly and children, who suffer from difficulty in swallowing tablets and can be administered to schizophrenia patients for a long period of time.

Hereinafter, the present invention will be explained in more detail with reference to the following examples. These examples are provided for illustrative purposes only and are not intended to limit the scope of the invention.

EXAMPLES

Films were produced to have the compositions shown in Table 1. Aripiprazole was used as a pharmaceutically active ingredient. Each of the films had a width of 22 mm, a length of 30 mm, and a thickness of 75 μm. The numerical values in Table 1 are parts by weight.

TABLE 1

| Ingredient | Ex. 1 | Ex. 2 | Ex. 3 | Ex. 4 | Ex. 5 | Ex. 6 | Ex. 7 | Ex. 8 | Comp. Ex. 1 | Comp. Ex. 2 | Comp. Ex. 3 |
|---|---|---|---|---|---|---|---|---|---|---|---|
| Aripiprazole | 30.00 | 30.00 | 30.00 | 30.00 | 30.00 | 30.00 | 30.00 | 30.00 | 30.00 | 30.00 | 30.00 |
| Citric acid | 0.50 | 0.40 | 0.30 | 0.20 | 1.00 | — | 0.45 | 0.7 | — | — | — |
| Tartaric acid | — | — | — | — | — | 0.20 | — | — | — | — | — |
| Polyethylene Glycol 400 | 3.00 | 3.00 | 3.00 | 3.00 | 3.00 | 3.00 | 3.00 | 3.00 | 3.00 | 3.00 | 3.00 |
| Glycerin | 3.00 | 3.00 | 3.00 | 3.00 | 3.00 | 3.00 | 3.00 | 3.00 | 3.00 | 3.00 | 3.00 |
| Sucralose | 0.84 | 0.84 | 0.84 | 0.84 | 0.84 | 0.84 | 0.84 | 0.84 | 2.00 | — | 0.84 |
| Acesulfame potassium | 1.08 | 1.08 | 1.08 | 1.08 | 1.08 | 1.08 | 1.08 | 1.08 | — | 2.00 | 1.08 |
| Xylitol | 0.84 | 0.84 | 0.84 | 0.84 | 0.84 | 0.84 | 0.84 | 0.84 | 0.84 | 0.84 | 0.84 |
| L-menthol | 0.40 | 0.40 | 0.40 | 0.40 | 0.40 | 0.40 | 0.40 | 0.40 | 0.40 | 0.40 | 0.40 |
| Polyvinyl alcohol | 15.00 | 15.00 | 15.00 | 15.00 | 15.00 | 15.00 | 15.00 | 15.00 | 15.00 | 15.00 | 15.00 |
| Hydroxypropyl methylcellulose-L | 38.34 | 38.34 | 38.34 | 38.34 | 38.34 | 38.34 | 38.34 | 38.34 | 38.34 | 38.34 | — |
| Hydroxypropyl methylcellulose-H | 7.00 | 7.00 | 7.00 | 7.00 | 7.00 | 7.00 | 7.00 | 7.00 | 7.00 | 7.00 | — |
| Xanthan gum | — | — | — | — | — | — | — | — | — | — | 7.00 |
| Gelatinized starch | — | — | — | — | — | — | — | — | — | — | 38.34 |

EXPERIMENTAL EXAMPLES

The following experiments were conducted on the films produced in Examples 1-8 and Comparative Examples 1-3.

Experimental Example 1: pH Measurements

[Measurement of pH of the Films]
15 mg of each of the films produced in Examples 1-8 and Comparative Examples 1-3 was dissolved in 10 ml of purified water and the pH of the solution was measured using a pH meter (827 pH lab, Metrohm).
[Measurement of Intra-Oral pH]
About 3 min after patients were instructed to take the films produced in Examples 1-8 and Comparative Examples 1-3, the intra-oral pH values were measured.
The intra-oral pH values were measured using pH papers. BTB test papers (pH 6.2-7.8) and CPR test papers (pH 5.0-6.6) available from Advantec were used as the pH papers for accurate pH measurement. The BTB and CPR test papers can minutely measure the pH values at intervals of 0.2 in the respective pH ranges. Each test paper was allowed to absorb saliva on the tongue and its color was then compared with reference colors. The pH value was determined from a reference color closest to the color of the test paper. When the colors of the two papers were different from each other, the two values were averaged. A lower intra-oral pH value indicates a higher acidity. In this manner, the intra-oral pH values of the films containing different amounts of citric acid were measured.
The results are shown in Table 2.

The relatively high pH values of the film of Comparative Example 3 are also believed to be due to the use of the different film base polymers.

Experimental Example 2: Dissolution Experiment

In accordance with Method 2 (paddle method) for dissolution testing described in the general test methods of the Korean Pharmacopoeia, each of the films of Examples 1-8 and Comparative Examples 1-3 was dissolved under the following conditions: 37±5° C., 50 rpm, pH 1.2, pH 4.0 buffer 900 ml. The solution was filtered and 5 ml of the filtrate was accurately sampled. The absorbance values of the sample solution and the reference solution were measured at around 249 nm and 325 nm in accordance with the method for absorbance measurement described in the general test methods of the Korean Pharmacopoeia. The absorbance values were compared to calculate a dissolution rate of the film. 708-DS, VK8000 (Agilent) was used as a dissolution testing system and Libra S70 (Biochrom) was used to measure the absorbance values.

Figure 2:
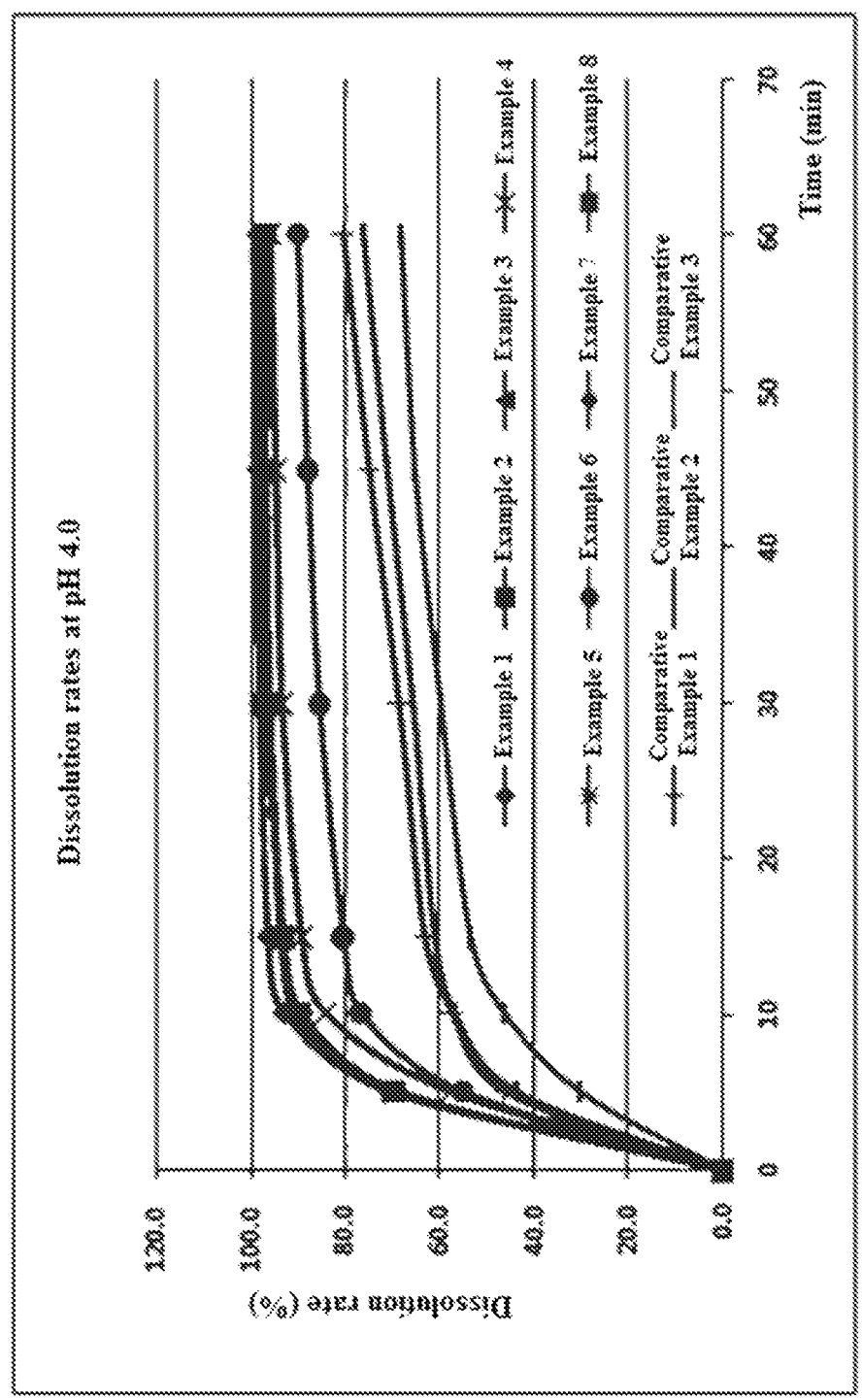
FIG. 2 is a graph showing the dissolution rates of orally fast dissolving film formulations produced in Examples 1-8 and Comparative Examples 1-3 at a pH of 4.0.

The experimental results are shown in FIGS. 1 and 2. From the results, the films of Examples 1-8 were confirmed to have higher dissolution rates than the films of Comparative Examples 1-3. Particularly, the dissolution rates of the comparative films in the acidic solution at pH 4.0 did not exceed 70% for 30 min. The film of Comparative Example

TABLE 2

| Ingredient | Ex. 1 | Ex. 2 | Ex. 3 | Ex. 4 | Ex. 5 | Ex. 6 | Ex. 7 | Ex. 8 | Comp. Ex. 1 | Comp. Ex. 2 | Comp. Ex. 3 |
|---|---|---|---|---|---|---|---|---|---|---|---|
| Film pH | 5.14 | 5.21 | 5.35 | 5.50 | 4.71 | 5.42 | 5.18 | 4.95 | 6.44 | 6.48 | 6.73 |
| Intra-oral pH | 6.4 | 6.4 | 6.5 | 6.8 | 5.8 | 6.6 | 6.3 | 6.2 | 7.3 | 7.3 | 7.8 |

As can be seen from the results in Table 2, the intra-oral pH tended to decrease with decreasing pH of the films. However, the pH of the films was not always in linear proportion to the intra-oral pH. These results are believed to be because the formulations were diluted with saliva secreted in the mouths. That is, when the effect of the citric acid to secrete saliva is significant, the intra-oral pH of each film is not greatly increased despite the low pH of the film.

3, which was produced using different film base polymers from those used in the films of Examples 1-8, had the lowest dissolution rates. Therefore, hydroxypropyl methylcellulose is believed to be advantageous in terms of dissolution rate.
Particularly, the higher dissolution rates of the films of Examples 1-8 at pH values of 1.2 and 4.0 indirectly demonstrate fast dissolution and absorption of the films in the stomach.

Experimental Example 3: Bitterness Masking Experiment

The films were organoleptically evaluated for taste. 20 panelists were requested to taste the films and the bitter taste was evaluated using a 5-point scale. The scores were rounded off to two decimal places.

The bitter taste was evaluated at the time when the panelists felt a bitter taste in their mouths. The taste was scored as "5" when the panelist felt a very bitter taste and as "1" when the bitter taste disappeared. Specifically, the taste was scored based on the following criteria: 1—excellent, 2—good, 3—fair, 4—poor, 5—very poor.

The results are shown in Table 3.

TABLE 3

| Ingredient | Ex. 1 | Ex. 2 | Ex. 3 | Ex. 4 | Ex. 5 | Ex. 6 | Ex. 7 | Ex. 8 | Comp. Ex. 1 | Comp. Ex. 2 | Comp. Ex. 3 |
|---|---|---|---|---|---|---|---|---|---|---|---|
| Taste | 2.2 (good) | 2.5 (good) | 2.5 (good) | 2.5 (good) | 2.2 (good) | 2.8 (good) | 2.5 (good) | 2.5 (good) | 4.1 (poor) | 4.3 (poor) | 3.0 (fair) |

Particularly, the film of Comparative Example 1 was bitter in foretaste and the film of Comparative Example 2 was bitter in aftertaste. The bitter taste of the film of Comparative Example 3 was not effectively masked by a sour taste and was felt stronger because saliva secretion was not sufficient, which are responsible for inferior evaluation results compared to the films of Examples 1-8.

Experimental Example 4: Stability Experiment

The films of Examples 1-8 and Comparative Examples 1-3 were tested for content stability and related substance content under extreme conditions (60° C., 75% RH) and accelerated conditions (40° C., 75% RH). The film was judged to have no problems in stability when the measurement results of the film were within the allowable range (95.0-105.0%). The films of Examples 1-8 and Comparative Examples 1-3 had no problems in content stability. The results are shown in Tables 3 and 4.

[Test Results for Content Stability]

TABLE 4

| Content reference 95.0-105.0% | Initial | 1 week under extreme conditions | 2 weeks under extreme conditions | 4 weeks under extreme conditions | 1 month under accelerated conditions |
|---|---|---|---|---|---|
| Example 1 | 101.1 | 100.7 | 100.2 | 102.0 | 102.0 |
| Example 2 | 100.8 | 99.9 | 100.5 | 100.0 | 100.5 |
| Example 3 | 100.4 | 101.2 | 100.7 | 101.4 | 100.0 |
| Example 4 | 100.3 | 101.1 | 101.7 | 100.6 | 101.2 |
| Example 5 | 99.9 | 100.2 | 98.8 | 99.4 | 100.6 |
| Example 6 | 98.7 | 99.6 | 98.3 | 100.6 | 99.0 |
| Example 7 | 100.5 | 99.6 | 100.2 | 99.7 | 99.7 |
| Example 8 | 100.4 | 101.2 | 100.8 | 101.0 | 100.5 |
| Comparative Example 1 | 99.1 | 100.9 | 100.2 | 98.8 | 98.1 |
| Comparative Example 2 | 102.1 | 100.4 | 101.9 | 102.6 | 101.8 |
| Comparative Example 3 | 101.5 | 101.7 | 100.0 | 102.9 | 100.6 |

[Test Results for Related Substance Content]

TABLE 5

| Reference Total amount of related substances: ≤1.0% | Initial | 1 week under extreme conditions | 2 weeks under extreme conditions | 4 weeks under extreme conditions | 1 month under accelerated conditions |
|---|---|---|---|---|---|
| Example 1 | N.D. | N.D. | N.D. | N.D. | N.D. |
| Example 2 | N.D. | N.D. | N.D. | N.D. | N.D. |
| Example 3 | N.D. | N.D. | N.D. | N.D. | N.D. |
| Example 4 | N.D. | N.D. | N.D. | N.D. | N.D. |
| Example 5 | N.D. | N.D. | N.D. | N.D. | N.D. |
| Example 6 | N.D. | N.D. | N.D. | N.D. | N.D. |

TABLE 5-continued

| Reference Total amount of related substances: ≤1.0% | Initial | 1 week under extreme conditions | 2 weeks under extreme conditions | 4 weeks under extreme conditions | 1 month under accelerated conditions |
|---|---|---|---|---|---|
| Example 7 | N.D. | N.D. | N.D. | N.D. | N.D. |
| Example 8 | N.D. | N.D. | N.D. | N.D. | N.D. |
| Comparative Example 1 | N.D. | 0.03 | 0.06 | 0.10 | 0.05 |
| Comparative Example 2 | N.D. | 0.04 | 0.08 | 0.13 | 0.04 |
| Comparative Example 3 | N.D. | 0.06 | 0.13 | 0.20 | 0.08 |

The data shown in Table 4 indicate that no related substances were detected in the films of Examples 1-8 in the initial stages, 4 weeks under the extreme conditions, and 1 month under the accelerated conditions. The test results for stability show that no related substances were increased in the films of Examples 1-8. In contrast, a slight increase in the total amount of related substances was observed in the films of Comparative Examples 1-3 with the passage of time. Therefore, it can be concluded that the fast dissolving films of Examples 1-8 are excellent in stability.

While the present invention has been described with reference to specific embodiments, the embodiments are merely illustrative and the present invention is not limited thereto. Those skilled in the art will appreciate that many modifications and variations can be made to the embodiments, without departing from the scope of the present invention as set forth in the appended claims. It is to be understood that such modifications and variations are encompassed within the scope of the present invention.

The invention claimed is:

1. An orally fast dissolving film formulation comprising aripiprazole or a pharmaceutically acceptable salt thereof and an organic acid, wherein:
the film formulation has a pH in the range of 4.95 to 5.18;
the aripiprazole or the pharmaceutically acceptable salt thereof and the organic acid have a weight ratio in the range of 2:1 to 66:1;
the organic acid is citric acid; and
the orally fast dissolving film formulation has a pH in the range of 6.2 to 6.4 when dissolved in an oral cavity.

2. The orally fast dissolving film formulation according to claim 1, wherein the citric acid is present in an amount of 0.2 to 1.0% by weight, based on the total weight of the orally fast dissolving film formulation.

3. The orally fast dissolving film formulation according to claim 1, further comprising a sweetening agent comprising sucralose and acesulfame potassium.

4. The orally fast dissolving film formulation according to claim 1, further comprising a film base polymer essentially comprising hydroxypropyl methylcellulose and optionally polyvinyl alcohol.

* * * * *